(12) United States Patent
Mese et al.

(10) Patent No.: US 10,963,320 B1
(45) Date of Patent: Mar. 30, 2021

(54) PRESENTING A HYGIENE WARNING

(71) Applicant: LENOVO (Singapore) PTE. LTD., New Tech Park (SG)

(72) Inventors: John Carl Mese, Cary, NC (US); Mark Patrick Delaney, Raleigh, NC (US); Nathan J. Peterson, Oxford, NC (US); Russell Speight VanBlon, Raleigh, NC (US); Arnold S. Weksler, Raleigh, NC (US)

(73) Assignee: Lenovo (Singapore) PTE. LTD., New Tech Park (SG)

( * ) Notice: Subject to any disclaimer, the term of this patent is extended or adjusted under 35 U.S.C. 154(b) by 0 days.

(21) Appl. No.: 16/833,136

(22) Filed: Mar. 27, 2020

(51) Int. Cl.
*G06F 9/54* (2006.01)
*H04W 4/021* (2018.01)
*G06F 3/0482* (2013.01)
*G06F 3/0488* (2013.01)

(52) U.S. Cl.
CPC ............ *G06F 9/542* (2013.01); *G06F 3/0482* (2013.01); *G06F 3/04883* (2013.01); *H04W 4/021* (2013.01)

(58) Field of Classification Search
CPC .................................. G06F 3/016; G06F 9/542
USPC .......................................... 719/318; 715/702
See application file for complete search history.

(56) References Cited

U.S. PATENT DOCUMENTS

| | | | | |
|---|---|---|---|---|
| 8,930,341 | B2 * | 1/2015 | Amin | G01N 33/0031 707/706 |
| 9,227,024 | B2 * | 1/2016 | Deutsch | A61M 5/5086 |
| 10,235,861 | B1 * | 3/2019 | Burns | G08B 21/02 |
| 2014/0301893 | A1 * | 10/2014 | Stroup | A61L 2/10 422/24 |
| 2017/0270267 | A1 * | 9/2017 | Muller-Wende | G06Q 50/22 |
| 2020/0126395 | A1 * | 4/2020 | Antolic-Soban | G08B 21/245 |

* cited by examiner

*Primary Examiner* — Andy Ho
(74) *Attorney, Agent, or Firm* — Kunzler Bean & Adamson

(57) ABSTRACT

For presenting a hygiene warning, a processor detects satisfying a risk policy. The risk policy is satisfied in response to a touch of an electronic device by a user. The processor presents a hygiene warning on the electronic device in response to satisfying the risk policy.

17 Claims, 6 Drawing Sheets

PRESENTING A HYGIENE WARNING

FIELD

The subject matter disclosed herein relates to hygiene warnings and more particularly relates to presenting a hygiene warning.

BACKGROUND

Electronic devices may become unhygienic through use.

BRIEF SUMMARY

An apparatus for presenting a hygiene warning is disclosed. The apparatus includes a processor and a memory that stores code executable by the processor. The processor detects satisfying a risk policy. The risk policy is satisfied in response to a touch of an electronic device by a user. The processor presents a hygiene warning on the electronic device in response to satisfying the risk policy. A method and program product also perform the functions of the apparatus.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Figure 1A:
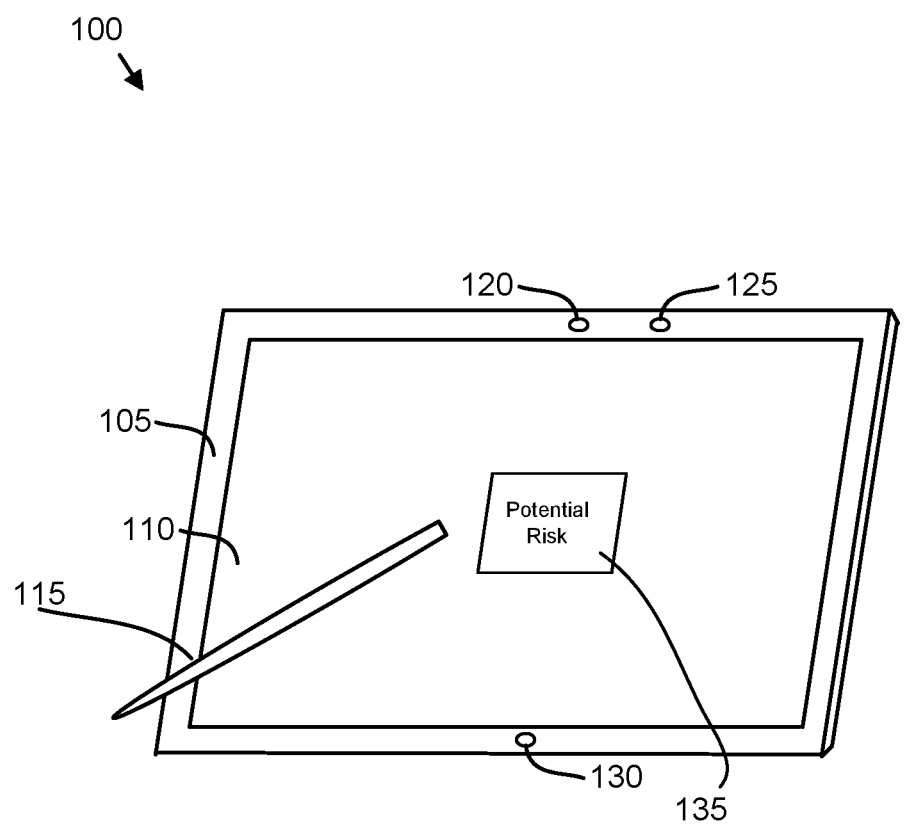
FIG. 1A is a perspective drawing illustrating one embodiment of a device system.

As will be appreciated by one skilled in the art, aspects of the embodiments may be embodied as a system, method or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Code for carrying out operations for embodiments may be written in any combination of one or more programming languages including an object oriented programming language such as Python, Ruby, R, Java, Java Script, Smalltalk, C++, C sharp, Lisp, Clojure, PHP, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise. The term "and/or" indicates embodiments of one or more of the listed elements, with "A and/or B" indicating embodiments of element A alone, element B alone, or elements A and B taken together.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. This code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

FIG. 1A is a perspective drawing illustrating one embodiment of a device system 100. In one embodiment, the device system 100 gathers user information such as patient information for a patient at a medical facility. In addition, the device system 100 may include electronic devices 105 for other uses, such as mobile telephones, electronic devices 105 for gathering customer user information, providing information and/or entertainment to customer users, and/or electronic devices 105 that are shared among family members.

In the depicted embodiment, the system 100 includes the electronic device 105 with a display 110. In addition, the electronic device 105 includes a camera 120, a speaker 125, and/or a microphone 130. The electronic device 105 may receive input via a stylus 115. In addition, the electronic device 105 may receive input via a keyboard presented on the display 110.

In the past, a user may employ the system 100 unaware that the system 100 was previously used by another person including a potentially contagious person without subsequent disinfection. The embodiments detect the satisfaction of a risk policy for the electronic device 105. The risk policy may be satisfied in response to a touch of the electronic device 105 by a user and/or other criteria. In response to the satisfaction of the risk policy, the embodiments present a hygiene warning 135. The hygiene warning 135 warns the potential user of the risk of using the system 100. In addition, the hygiene warning 135 may prompt for the disinfection of the system 100. As a result, the unintentional spread of disease may be mitigated.

Figure 1B:
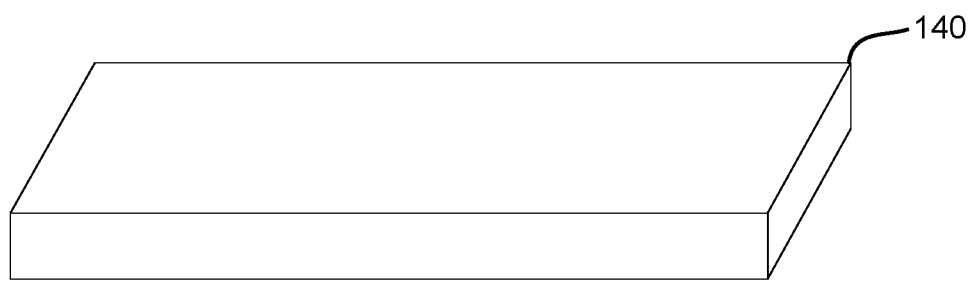
FIG. 1B is a perspective drawing illustrating one embodiment of a disinfection device.

FIG. 1B is a perspective drawing illustrating one embodiment of the disinfection device 140. The disinfection device 140 may be used to disinfect the system 100 and/or electronic device 105. In the depicted embodiment, the disinfection device 140 is an ultraviolet disinfector. In one embodiment, the system 100 is placed within the disinfection device 140 and exposed to ultraviolet light, killing potential pathogens. Additional disinfection devices 140 may include wipes and/or sprays.

In one embodiment, the electronic device 105 may be paired to the disinfection device 140. The disinfection device 140 may detect that the electronic device 105 is placed within the disinfection device 140. The disinfection device 140 may further communicate to the electronic device 105 that the electronic device 105 and/or system 100 has been disinfected.

Figure 2:
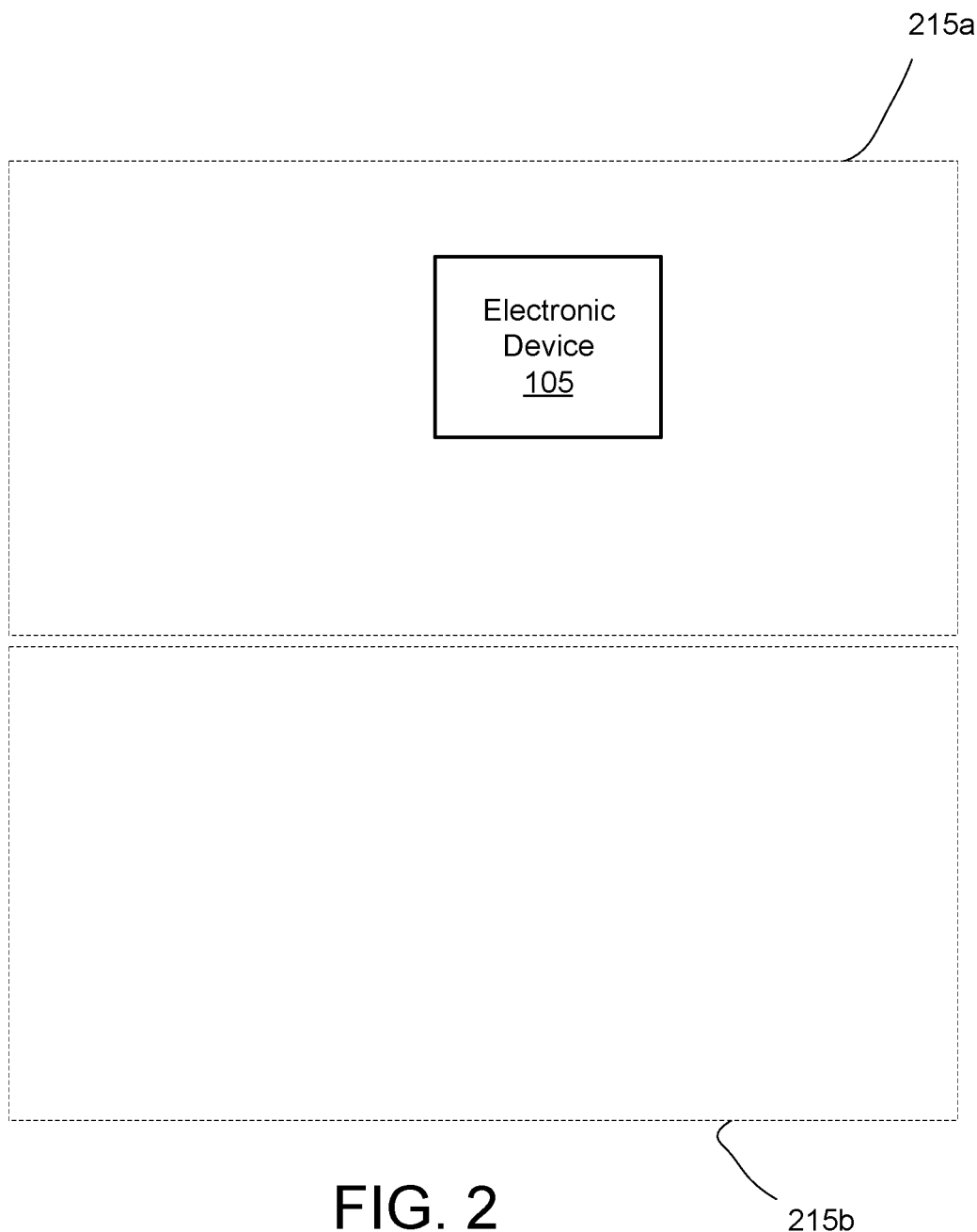
FIG. 2 is a schematic block diagram illustrating one embodiment of a geo-fence.

FIG. 2 is a schematic block diagram illustrating one embodiment of a geo-fence 215. In the depicted embodiment, two geo-fences 215 are shown. Each geo-fence 215 may demark a specified physical area. For example, a first geo-fence 215a may demark a storage area and/or preparation area. In addition, a second geo-fence 215b may demark a waiting room area. The geo-fences 215 may be demarked by wireless signals, infrared signals, position coordinates, and the like.

In one embodiment, the electronic device 105 determines that the electronic device 105 is within a first geo-fence 215a. The electronic device 105 may further identify that the electronic device 105 transitions to a second geo-fence 215b. In one embodiment, the transition between geo-fences 215 may satisfy the risk policy.

Figure 3:
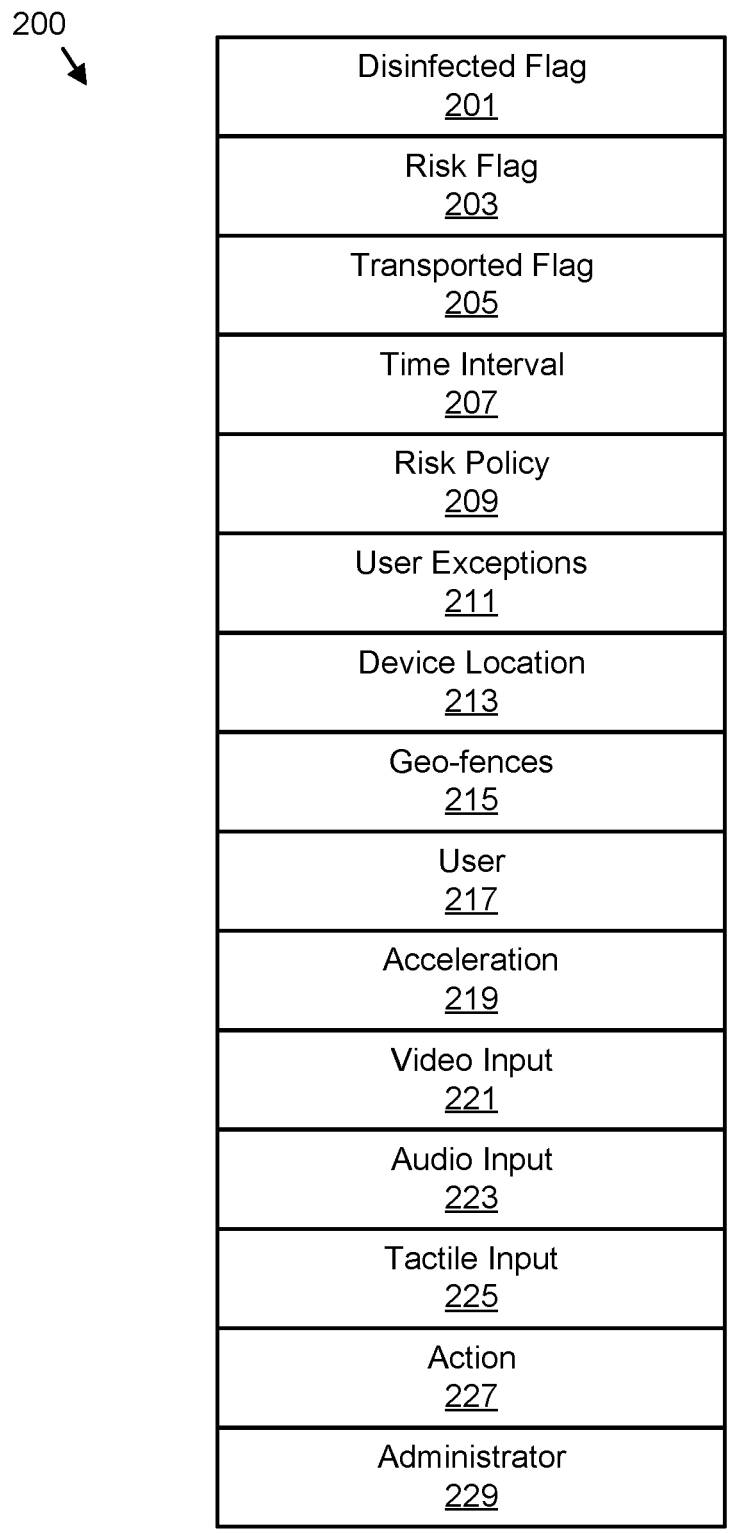
FIG. 3 is a schematic block diagram illustrating one embodiment of risk data.

FIG. 3 is a schematic block diagram illustrating one embodiment of risk data 200. The risk data 200 may be used to determine whether to present the hygiene warning 135. The risk data 200 may be organized as a data structure in a memory. In the depicted embodiment, the risk data 200 includes a disinfected flag 201, a risk flag 203, a transported flag 205, a time interval 207, the risk policy 209, user exceptions 211, a device location 213, the geo-fences 215, one or more users 217, an acceleration 219, a video input 221, an audio input 223, a tactile input 225, an action 227, and an administrator 229.

The disinfected flag 201 may be set in response to the electronic device 105 and/or system 100 being disinfected. In one embodiment, the disinfected flag 201 is set by the disinfection device 140. The disinfection device 140 may direct the electronic device 105 to set the disinfected flag 201 after the system 100 is disinfected by the disinfection device 140.

The risk flag 203 may be set in response to satisfying the risk policy 209. In one embodiment, the risk flag 203 is cleared when the disinfected flag 201 is set. In addition, the disinfected flag 201 may be cleared in response to the risk flag 203 being set.

The transported flag 205 may be set in response to determining that the system 100 and/or electronic device 105 moves outside a geo-fence 215. In addition, the transported flag 205 may be set in response to the system 100 and/or electronic device 105 moving into a geo-fence 215. In a certain embodiment, the transported flag 205 is set in response to determining that the system 100 and/or electronic device 105 moves between geo-fences 215.

The time interval 207 may record an elapsed time. The elapsed time may be measured from disinfecting the system 100, transitioning geo-fences 215, and the like.

The risk policy 209 may determine when the system 100 and/or electronic device 105 is a potential risk to users 217. In addition, the risk policy 209 may determine if the hygiene warning 135 should be presented. The criteria for satisfying the risk policy 209 are described hereafter.

The user exceptions 211 may specify one or more users that may employ the system 100 and/or electronic device 105 without satisfying the risk policy 209. For example, the spouse of the user 217 may be a user exception 211. As a result, the spouse may use the electronic device 105 without satisfying the risk policy 209.

The device location 213 specifies a current location of the electronic device 105 and/or system 100. In one embodiment, the device location 213 maintains a history of locations for the electronic device 105 and/or system 100.

The geo-fences 215 define areas that the system 100 may be within, may move out of, and/or may move into. The geo-fences 215 may be defined by wireless signals. For example, if the specified wireless signal is detectable, the electronic device 105 may be within a geo-fence 215. In addition, the geo-fence 215 may be defined by infrared signals. For example, if the specified infrared signal is detected, the electronic device 105 may be transitioning between geo-fences 215. In one embodiment, a geo-fence 215 is defined by a series of coordinates that specify the area of the geo-fence 215.

The user 217 may identify one or more users of the system 100 and/or electronic device 105. In one embodiment, the users 217 are identified with a time interval 207. In addition, users 217 may be identified by name and/or an identification number. In a certain embodiment, users 217 may be identified as owner users 217 and nonowner users 217.

The acceleration 219 may record one or more accelerations of the electronic device 105. The acceleration 219 may be used to determine if the electronic device 105 was used. In a certain embodiment, the acceleration 219 is used to determine the device location 213.

The video input 221 may record video from the camera 120. The audio input 223 may record input from the microphone 130. The tactile input 225 may record input from the display 110.

The action 227 may record one or more actions performed by a user 217 of the electronic device 105. In one embodiment, the action 227 is selected from the group consisting of coughing and sneezing.

The administrator 229 may identify a person responsible for maintaining the system 100 and/or electronic device 105. In one embodiment, the administrator 229 may clear the risk flag 203 and/or set the disinfected flag 201. In addition, the administrator 229 may set the risk flag 203 and/or clear the disinfected flag 201. The administrator 229 may be identified by a login and/or a biometric.

Figure 4A:
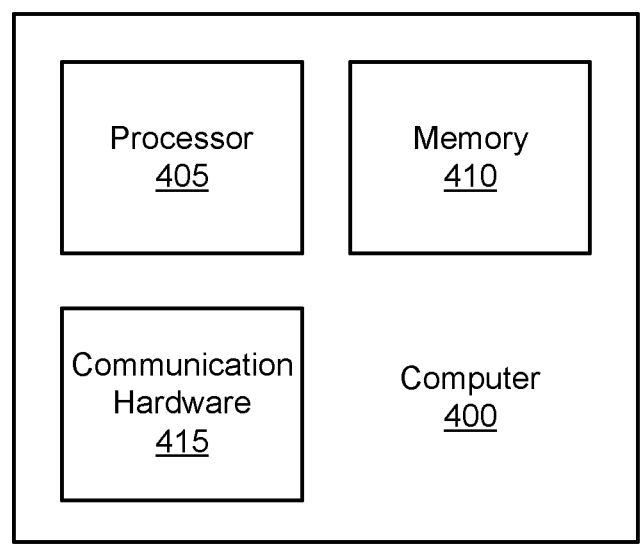
FIG. 4A is a schematic block diagram illustrating one embodiment of a computer.

FIG. 4A is a schematic block diagram illustrating one embodiment of a computer 400. The computer 400 may be embodied in the electronic device 105. In the depicted embodiment, the computer 400 includes a processor 405, a memory 410, and communication hardware 415. The memory 410 may comprise a semiconductor storage device, a hard disk drive, or combinations thereof. The memory 410 may store code. The processor 405 may execute the code. The communication hardware 415 may communicate with other devices such as the disinfection device 140.

Figure 4B:
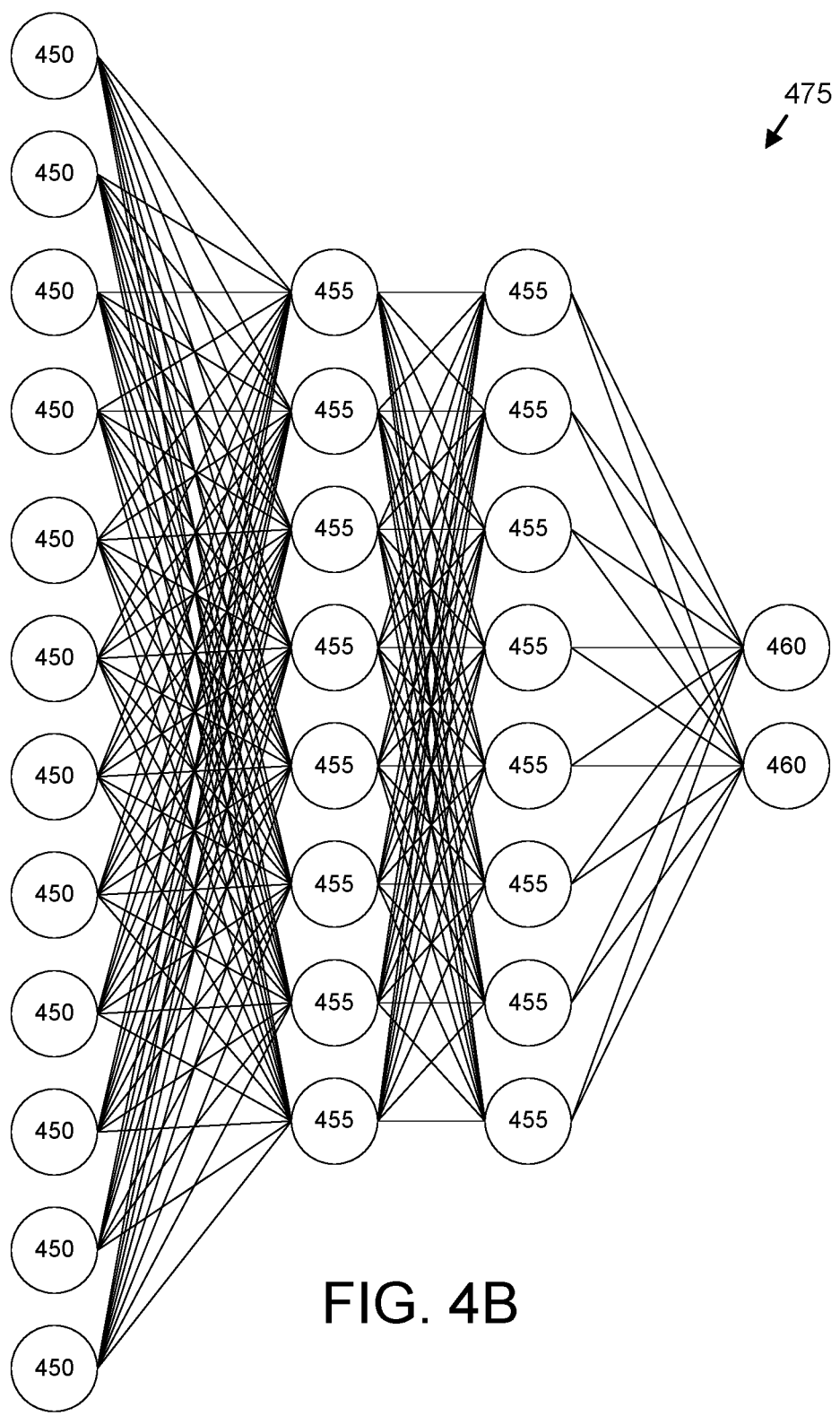
FIG. 4B is a schematic diagram illustrating one embodiment of a neural network.

FIG. 4B is a schematic diagram illustrating one embodiment of a neural network 475. In the depicted embodiment, the neural network 475 includes input neurons 450, hidden neurons 455, and output neurons 460. The neural network 475 may be organized as a convolutional neural network, a recurrent neural network, long short term memory network, and the like.

The neural network 475 may be trained with training data. The training data may include a plurality of risk data 200 and an indication of whether the risk policy 209 is satisfied, an indication of whether the disinfected flag 201 should be set or cleared, and/or an indication of whether the risk flag 203 should be set or cleared. In a certain embodiment, the training data indicates whether the transported flag 205 should be set or cleared. The neural network 475 may be trained using one or more learning functions while applying the training data to the input neurons 450 and known result values for the output neurons 460. Subsequently, the neural network 475 may receive actual data at the input neurons 450 and make predictions at the output neurons 460 based on the actual data. The actual data may include data from the current risk data 200. The neural network 475 may determine whether the risk policy 209 is satisfied, whether to set or clear the disinfected flag 201, whether to set or clear the risk flag 203, and/or whether to set or clear the transported flag 205 based on the current risk data 200.

Figure 5:
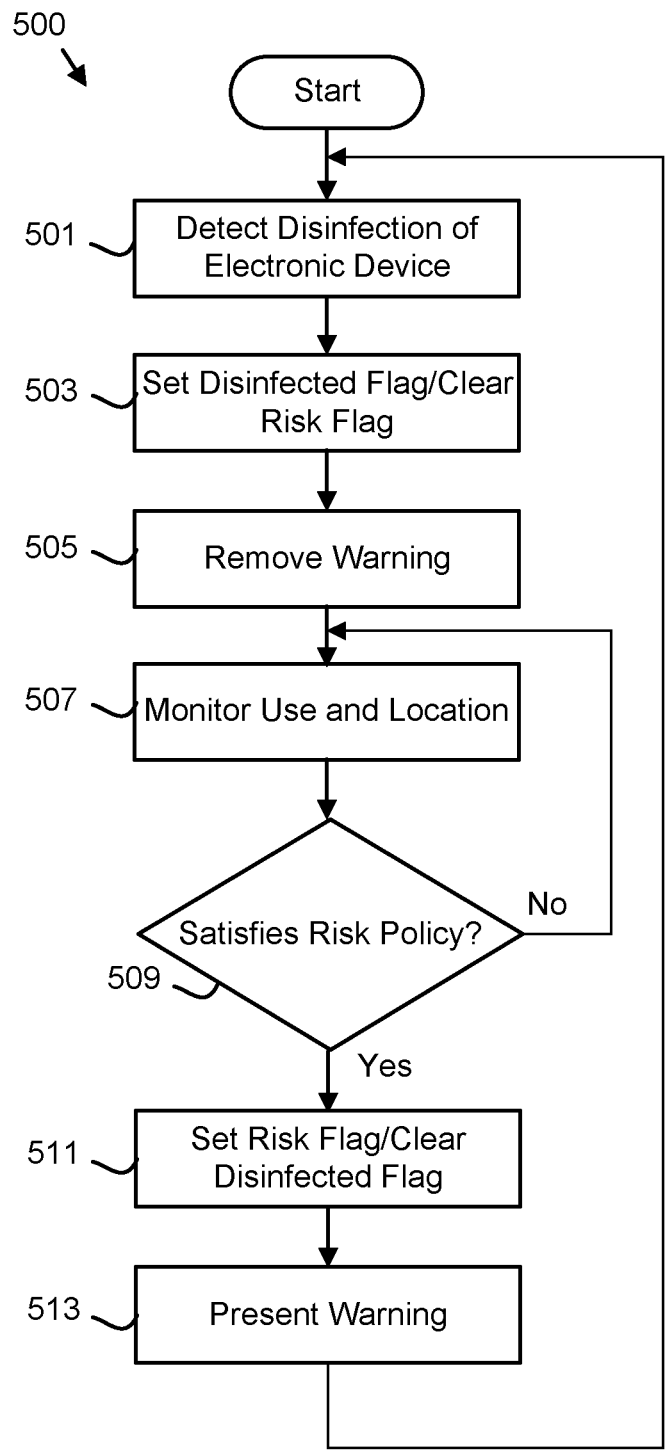
FIG. 5 is a schematic flow chart diagram illustrating one embodiment of a hygiene warning method.

FIG. 5 is a schematic flow chart diagram illustrating one embodiment of a hygiene warning method 500. The method 500 may detect satisfaction of the risk policy 209 and present the hygiene warning 135. The method 500 may be performed by the electronic device 105, the computer 400, and/or the processor 405.

The method 500 starts, and in one embodiment, the processor 405 detects 501 the disinfection of the electronic device 105 and/or system 100. The disinfection may be detected 501 in response to a communication from the paired disinfection device 140. In addition, the disinfection may be detected 501 in response to an input from the administrator 229. The administrator 229 may be identified by a login and/or a biometric. For example, the administrator 229 may wipe the electronic device 105 and/or system 100 with disinfectant that then use a biometric to verify that the electronic device 105 and/or system 100 was disinfected.

The processor 405 may set 503 the disinfected flag 201 and/or clear the risk flag 203 in response to detecting 501 the disinfection of the electronic device 105 and/or system 100. In addition, the processor 405 may remove 505 the hygiene warning 135 in response to detecting 501 disinfection of the electronic device 105.

The processor 405 may monitor 507 the use and/or the location of the system 100 and/or electronic device 105. In one embodiment, the processor 405 monitors 507 the acceleration 219, the video input 221, the audio input 223, and/or the tactile input 225 to the electronic device 105. In addition, the processor 405 may monitor 507 the device location 213.

In one embodiment, the processor 405 monitors 507 and identifies each user 217 of the electronic device 105 and/or system 100. The processor 405 may further monitor 507 the crossing of geo-fences 215. The processor 405 may monitor 507 the time interval 207 associated with each user 217, geo-fence 215, device location 213, acceleration 219, video input 221, audio input 223, and/or tactile input 225.

The processor 405 may determine 509 whether the risk policy 209 is satisfied. In one embodiment, the risk policy 209 is satisfied in response to a touch of the electronic device 105 by a user 217. For example, if any user 217 employs the system 100 and/or electronic device 105, the risk policy 209 may be satisfied.

In one embodiment, the touch is determined from the tactile input 225. For example, if the user 217 employs the stylus 115 and/or a keyboard in the display 110, the processor 405 may determine a touch.

In one embodiment, the touch is determined from the acceleration 219. For example, the touch may be determined from acceleration 219 of the electronic device 105 consistent with use. In a certain embodiment, the touch is determined from acceleration 219 for a specified time interval 207.

In a certain embodiment, the risk policy 209 is satisfied in response to use by a non-owner user 217. For example, if an owner user 217 employs the system 100 and/or electronic device 105, the risk policy 209 may not be satisfied. However, if the non-owner user 217 employs the system 100 and/or electronic device 105, the risk policy 209 may be satisfied. In a certain embodiment, the risk policy 209 is not satisfied in response to a user 217 listed in the user exceptions 211 implying the system 100 and/or electronic device 105. For example, if a spouse user 217 of the owner user 217 is listed as a user exception 211 and employs the system 100 and/or electronic device 105, the risk policy 209 may not be satisfied.

In one embodiment, the processor 405 detects touch of a system element such as the stylus 115 by a user. For example, 120 may capture video input 221 of a user handling the stylus 115.

In one embodiment, the risk policy 209 is satisfied in response to the electronic device 105 and/or system being in proximity to a user 217. For example, the processor 405 identify the user 217 from the video input 221. The risk policy 209 may be satisfied in response to the user 217 being within a specified distance of the camera 120 and/or electronic device 105. The risk policy 209 may be satisfied in response to the user 217 being within a specified distance of the camera 120 and/or electronic device 105 for a specified time interval 207.

The risk policy 209 may be satisfied in response to the electronic device 105 crossing a geo-fence 215. For example, the risk policy 209 may be satisfied if the electronic device 105 crosses into a geo-fence 215 defining a waiting room. The processor 405 may monitor the device location 213 to determine when the system 100 and/or electronic device 105 crosses the geo-fence 215.

The risk policy 209 may be further satisfied in response to detecting the action 227. For example, the processor 405 may detect coughing from the video input 221 and/or the audio input 223. In addition, the processor 405 may detect sneezing from the video input 221 and/or the audio input 223. Detecting the action 227 may satisfy the risk policy 209.

The risk policy 209 may be satisfied based on the acceleration 219, the video input 221, the audio input 223, and/or the tactile input 225. For example, the neural network 475 may identify combinations of the acceleration 219, the video input 221, audio input 223, and/or tactile input 225 associated with the risk policy 209 being satisfied.

In one embodiment, the risk policy 209 is satisfied in response to the disinfected flag 201 not been set. As a result, the hygiene warning 135 may be presented as a default unless the system 100 and/or electronic device 105 is disinfected.

If the risk policy 209 is not satisfied, the processor 405 continues to monitor 507 the use and location of the system 100 and/or electronic device 105. If the risk policy 209 is satisfied, the processor 405 may set the risk flag 203. In addition, the processor 405 may clear the disinfected flag 201.

The processor 405 further presents 513 the hygiene warning 135 in response to the satisfaction of the risk policy 209 and the method 500 ends. The hygiene warning 135 may be presented on the display 110. In a certain embodiment, an audible hygiene warning 135 is presented via the speaker 125 in response to detecting the touch of the system 100 and/or electronic device 105. For example, the audible hygiene warning 135 may be presented in response to detecting acceleration 219 of the electronic device 105.

The embodiments detect the satisfaction of the risk policy 209. A touch of the electronic device 105 by a user 217 may satisfy the risk policy 209. The embodiments further present the hygiene warning 135 on the electronic device 105 in response to the satisfaction of the risk policy 209. As a result, user 217 is warned if the electronic device 105 and/or system 100 was previously used by a potentially contagious and/or infectious person. Thus the user 217 of the system is protected from potential infection and/or contamination.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
   a processor;
   a memory that stores code executable by the processor to:
   detect satisfying a risk policy, wherein the risk policy is satisfied in response to a touch of an electronic device by a nonowner user, wherein the electronic device comprises a camera and a stylus and the camera identifies the nonowner user touching the stylus;
   present a hygiene warning on the electronic device in response to satisfying the risk policy; and
   remove the hygiene warning in response to detecting disinfection of the electronic device.

2. The apparatus of claim 1, wherein disinfection is detected in response to a communication from a paired disinfection device.

3. The apparatus of claim 1, wherein disinfection is detected in response to input from an administrator identified by a login and/or a biometric.

4. The apparatus of claim 1, wherein the risk policy is further satisfied in response to the electronic device being in proximity to the user.

5. The apparatus of claim 1, wherein the risk policy is further satisfied in response to the electronic device crossing a geofence.

6. The apparatus of claim 1, wherein the risk policy is further satisfied in response to detecting an action selected from the group consisting of coughing and sneezing.

7. The apparatus of claim 1, wherein the risk policy is further satisfied based on an acceleration, a video input, an audio input, and/or a tactile input.

8. The apparatus of claim 1, wherein the risk policy is further satisfied in response to a disinfected flag not being set.

9. A method comprising:
   detecting, by use of a processor, satisfying a risk policy, wherein the risk policy is satisfied in response to a touch of an electronic device by a nonowner user, wherein the electronic device comprises a camera and a stylus and the camera identifies the nonowner user touching the stylus;
   presenting a hygiene warning on the electronic device in response to satisfying the risk policy; and
   removing the hygiene warning in response to detecting disinfection of the electronic device.

10. The method of claim 9, wherein disinfection is detected in response to a communication from a paired disinfection device.

11. The method of claim 9, wherein disinfection is detected in response to input from an administrator identified by a login and/or a biometric.

12. The method of claim 9, wherein the risk policy is further satisfied in response to the electronic device being in proximity to the user.

13. The method of claim 9, wherein the risk policy is further satisfied in response to the electronic device crossing a geofence.

14. The method of claim 9, wherein the risk policy is further satisfied in response to detecting an action selected from the group consisting of coughing and sneezing.

15. The method of claim 9, wherein the risk policy is further satisfied in response to use by a nonowner user.

16. The method of claim 9, wherein the risk policy is further satisfied based on an acceleration, a video input, an audio input, and/or a tactile input.

17. A program product comprising a computer readable storage medium that stores code executable by a processor, the executable code comprising code to:
   detect satisfying a risk policy, wherein the risk policy is satisfied in response to a touch of an electronic device by a nonowner user, wherein the electronic device comprises a camera and a stylus and the camera identifies the nonowner user touching the stylus;
   present a hygiene warning on the electronic device in response to satisfying the risk policy; and
   remove the hygiene warning in response to detecting disinfection of the electronic device.

* * * * *